Figure 1:
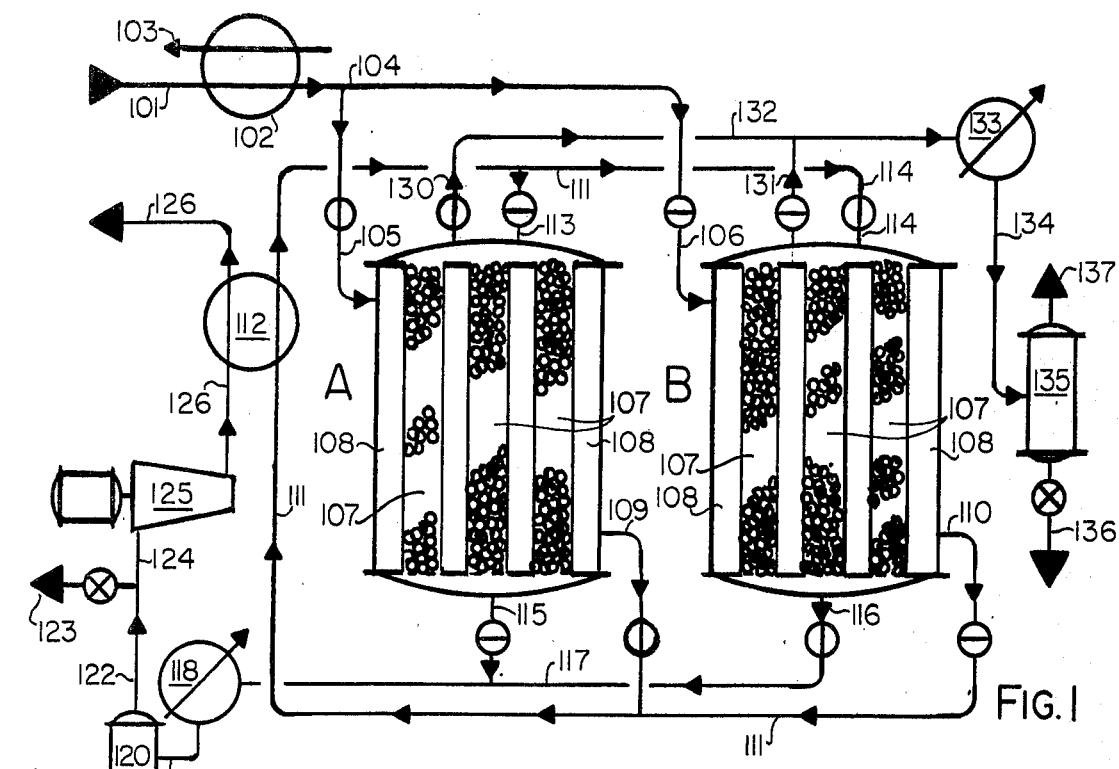

United States Patent [19]

Othmer

[11] 4,405,343

[45] Sep. 20, 1983

[54] METHANOL DEHYDRATION

[76] Inventor: Donald F. Othmer, 333 Jay St., Brooklyn, N.Y. 11201

[21] Appl. No.: 413,744

[22] Filed: Sep. 1, 1982

[51] Int. Cl.³ ............................................. B01D 53/04
[52] U.S. Cl. ............................................. 55/28; 55/33; 55/35; 55/58; 55/68; 55/74; 55/75
[58] Field of Search ....................................... 55/25–28, 55/30, 31, 33, 35, 58, 62, 68, 74, 75, 163, 179, 387, 389; 203/18; 568/916, 917

[56] References Cited

U.S. PATENT DOCUMENTS

| | | | |
|---|---|---|---|
| 1,985,205 | 12/1934 | Derr | 55/35 |
| 2,137,605 | 11/1938 | Derr | 55/33 |
| 2,472,912 | 6/1949 | McCarter | 568/916 X |
| 2,847,480 | 8/1958 | Kaiser | 568/917 |
| 2,882,243 | 4/1959 | Milton | 568/917 X |
| 2,882,244 | 4/1959 | Milton | 568/917 X |
| 3,122,486 | 2/1964 | Skarstrom | 203/18 |
| 4,273,621 | 6/1981 | Fornoff | 568/916 X |
| 4,277,635 | 7/1981 | Oulman et al. | 568/916 |
| 4,319,057 | 3/1982 | Kiser | 568/916 |
| 4,351,732 | 9/1982 | Psaras et al. | 55/208 X |

FOREIGN PATENT DOCUMENTS

| | | | |
|---|---|---|---|
| 2263995 | 10/1975 | France | 568/917 |
| 240694 | 4/1969 | U.S.S.R. | 568/916 |

Primary Examiner—Robert H. Spitzer

[57] ABSTRACT

Methanol is converted from syngas at high temperatures and pressures. The gas stream leaving the converter, at 300° to 500° C., above atmospheric pressure—usually between 750 to 7000 pounds per square inch, has besides the unreacted permanent gases of the syngas and others, methanol and water as well as other liquid impurities. Based on the weight of methanol, water may be present in from 0.5 to 20%, also small amounts of higher alcohols, dimethyl ether, etc. Condensation gives an aqueous liquid, from which the water must be separated if the methanol is to be used as a motor fuel. When this amount of water is low e.g. 0.5 to 12% this may be separated by adsorption most economically from the gas before condensation of the methanol. The energy in this gas stream at a high temperature and pressure above the ambient may be used to dehydrate completely the methanol, by the use of a conventional desiccant.

21 Claims, 2 Drawing Figures

METHANOL DEHYDRATION

The process of this invention separates a relatively small amount of water from a hot gas mixture containing, besides permanent gases, mostly methanol. Often it contains other vapors also as small amounts of some higher alcohols.

This method is particularly useful in removing water from the gas mixture from a converter producing synthetic methanol, when the methanol is to be used in admixture with gasoline as a motor fuel, or when for other reasons it must be rigorously anhydrous. Water formed with the methanol as a by-product in its synthesis from hydrogen and one or both carbon oxides prevents the complete miscibility with gasoline which is necessary when used in automobiles. It may also be used in dehydrating other gas streams containing methanol and a relatively small amount of water as vapors.

In making synthetic methanol, conventional practice has produced a hot gas stream having vapors of methanol and as much as 20% water based on the methanol content. This water is obtained in the product on the condensation of the vapors in the gas leaving the catalytic converter. Modern processing has reduced this to 10% in many cases, and in U.S. Pat. No. 4,235,799, the amount of water present may be less than 1%. This is based on methanol produced, as is the somewhat less than 2 or 3% of higher alcohols, principally ethyl. Also dimethyl ether is in the gas stream formed in the converter, and these organics may be condensed along with the methanol and water and the mixture used directly as a fuel. The water alone must be separated if the liquid is to be mixed with gasoline.

Methanol has long been separated from water by distillation with rectification. All of the methanol (b.p. 65° C.) is readily distilled—with reflux—away from the water; and this may be the most economical separation method when 15 to 20% water is present. However, when the water is present in smaller amounts, i.e. 0.5 to 10 or 12%, and especially when present in an amount of from 0.05% to 2%, the distillation of all of the methanol away from the small amount of water requires a substantial amount of heat and a large distillation system compared to the adsorption system of the present invention.

Fractional adsorption of the small amount of water away from the methanol has been found to use much less energy. Then for fuel use, the methanol requires no distillation or other refining, as the other impurities the higher alcohols, and other organics are also good fuels. Also, in the dehydration of the methanol vapors present in the gas stream leaving the catalytic converter at a pressure and temperature above the ambient, it has been found that the use of some part of the heat contained in these vapors above the ambient temperature may be used for the regeneration of the adsorbent material, always an essential step in any continuous adsorption operation.

The several processes for converting syngas to methanol discharge a hot gas stream from the converter containing from 3 to 25 mol % methanol and at a pressure of from 750 to 7000 pounds per square inch gage and a temperature of from 300° C. to 500° C. The thermal and mechanical energy in this gas stream at these high pressures and temperatures compared to the ambient have been found usually to be more than adequate to supply the energy needs of the separating process for water, the subject of this invention.

In the operation of some converters, e.g. that of U.S. Pat. No. 4,235,799, the high temperature of the hot gas stream is reduced by transfer of some of its heat in a steam generator, and the steam so produced gives mechanical and or electrical power. It has been found that the energy so developed in cooling the hot gas stream may be at least sufficient to drive the pumps, compressors, etc used as essential accessories in this separation process. This energy is principally the heat at the high temperature of these gases—or even after being cooled somewhat in the steam generator. It has been found to be sufficient to accomplish the desorption operation either by heat transfer through the walls of the adsorber of by heating an inert gas which circulates in direct contact with the desiccant particles. More energy may be available than may be so required; and this energy coming from the steam generator may be used in other parts of the plant of which this process is a part. The hot gas stream may be cooled to as low a temperature as 25° C. before being dehydrated, as an aid thereto, so as to improve the dehydration. Other cooling agents than boiling water would then be used in other heat exchangers.

OBJECT OF THE INVENTION

It is thus the object of this invention, which may be accomplished readily, to separate the water from methanol and other vapors or gases which come from methanol synthesis in a converter at a superatmospheric pressure and a temperature between about 300° and 600° C. and with or without some cooling in a heat exchanger. Selective adsorption of the water present is accomplished, using some part of the sensible heat of the gas stream for generating mechanical and/or electrical energy and for heating of the adsorbent bed for regeneration of the adsorbent or desiccant through evaporation of the adsorbed water so that no energy from outside the system is added or required for operating this dehydration.

Adsorbent—Desiccants

Numerous solid materials have the ability to adsorb water vapor from a gas stream at various temperatures and pressures; and some of these desiccants may have more or less advantages when used in the present process.

In general, the particle size of a solid desiccant may be from that of a powder to that of a bead or pellet of any shape and having an average diameter of up to ⅛ to ¼ inch or even larger. Desireable particle size for optimum usefulness depends largely on mechanical considerations, the design and configuration of the adsorber bed or container, the method of support of the desiccant particles therein, the ease of flow of gas through such a bed, etc.

Such adsorbents or desiccants depend on a chemical and/or a physical attraction for the water molecule. When any amount of water is held by a solid desiccant, this water has a vapor pressure at every temperature which is very much reduced from the normal vapor pressure of water at that temperature. This vapor pressure increases with increasing amounts of water held, up to the maximum or saturation amount of the desiccant. For any constant amount of water or other fluid which has been adsorbed, the vapor pressure relations with temperature follow the same laws as for a pure substance (see for example, Othmer and Sawyer, Industrial & Engineering Chemistry Vol. 35, p. 1269, 1943).

The vapor pressure of the adsorbed water comes to equilibrium with that in the moist gas by adsorption of water therefrom, until the partial pressure of water in the gas is equal to the vapor pressure of the water adsorbed in the desiccant.

Regeneration, drying, or dewatering of the desiccant which has taken up water, is accomplished by (a) heating to a higher temperature (b) reducing the pressures (c) passing a stream of dry gas, or (d) passing a stream of gas containing a compound preferentially adsorbed by the solid. In the first three of these methods, regeneration of the desiccant is such as to give the water adsorbed a higher vapor pressure than that in the surroundings, so the water vaporizes. A combination of two or more of these methods of regeneration may be used.

A consideration of this vapor pressure of water from the desiccant explains why it is desirable that the adsorption—in some sense a type of condensation—of water from any gas stream carrying a fixed percentage of water can be more complete if the adsorption is conducted at a lower temperature, and/or a higher pressure. Correspondingly the regeneration is better at a higher temperature and/or a lower pressure.

In the condensation or adsorption of the water on the desiccant there is involved not only the usual latent heat of condensation of the water, but also the physical or chemical heat of the adsorption process. Both heats are involved likewise in the regeneration or evaporation of water from the desiccant.

The effectiveness of any desiccant is measured by the amount of water it will take up at any given temperature when its vapor pressure is in equilibrium with the partial pressure of water in the gas stream at a desired operating temperature. Other considerations are also very important, e.g. stability in repeated cycles of use and regeneration, inertness to other gases in the stream, mechanical strength to minimize breakage and crumbling, cost, etc.

Various solids have been found to have a greater or less extent the properties required in this process depending on the particular conditions involved, for example:—calcium sulfate, activated alumina, silica gel, and zeolites (aluminosilicates with alkali metal cations), among others. The first three may be less useful in some cases because of operating temperature ranges, or inefficiencies in separation in the presence of other components of the gas mixtures.

The so called "soluble" form of calcium sulfate (trade name Drierite) is a low cost desiccant which has been found useful when the range of adsorption temperature desired is at about 30° to 50° C. and the desorption is to be accomplished at 190° to 220° C. This low temperature range of adsorption gives at 30° C. an equilibrium moisture content in the gas stream of only about 0.005 milligrams of water per liter gas with a water adsorption of a little over 6%. However with a slightly less efficient water removal, this desiccant will remove up to 12 or 14% water by weight before regeneration is necessary.

Activated alumina has been found to give comparable drying to calcium sulfate for the gas at temperatures near the ambient but with a slightly higher capacity before regeneration at 150° to 300° C.

The zeolites desiccants are usually called Molecular Sieves. They have a crystalline structure, synthesized so as to give pores of a specific, uniform size which will admit and hold molecules of a definite size, and reject molecules of other sizes. They have been found to be particularly efficient in the process of this invention because of their selectivity for water also because of other properties than simply accepting a molecule of the size, the water molecule. These include their capability of holding large amounts of water with very low vapor pressures out of the desiccant and their stability over many cycles of dehydration and regeneration.

Different manufacturers provide standard grades of molecular sieves in powders and pellets or beads. All types have been found to be excellent desiccants in this use, with long service lives, particularly in the beads of screen mesh sizes of $4 \times 8$ or $8 \times 12$, or pellets of 1/16" or $\frac{1}{8}$" diameter, especially of type 3A and 13X.

They have been used at higher temperatures than other desiccants in this service; and capacities have been found to be over 15% by weight of water adsorbed even at 100° C.—somewhat less at 150° C., and extremely low residual water in the gas stream. Regeneration has been at temperatures of 200° to 350° C.

THE FIGURES

The Figures are entirely diagramatic flow sheets and have no scale. The various valves indicated are assumed to be opened and closed as required, either manually or automatically, in the sequence which will allow the desired flow of gases, principally, also of liquids. Valves are indicated by small circles, with one diameter drawn. If this is in line with the flow, the valve is open, if at right angles the valve is closed. If the valve has a pair of crossed diameters, this indicates that the valve may either be throttled or opened for only part of the time of the operation. The process, as represented by these flows is described by indication of the movements of the various fluid streams.

The adsorbent, preferably in the form of pellets or particles, rather that powder is charged loosely so as to fill the volume of the adsorber chambers, as shown by the aggregate of small circles.

FIG. 1 illustrates the operation which regenerates the adsorbent by a thermal-swing, with indirect heat transfer to the adsorbent bed, or a pressure-swing, or both.

Figure 2:
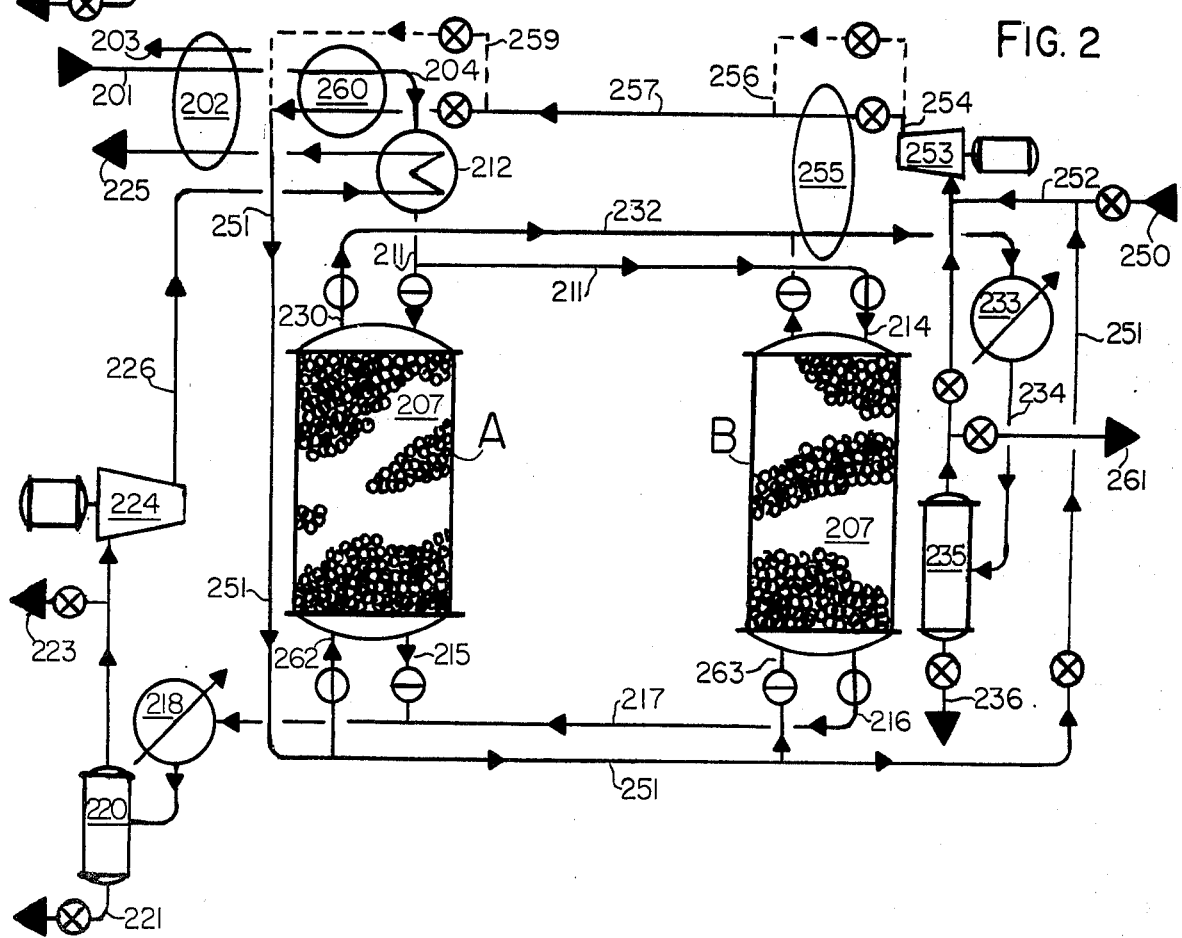

FIG. 2 details part of the flow sheet using a regenerative gas, herein called an inert gas, with or without a temperature-switch obtained by using a hot inert gas, and/or a pressure swing obtained by the use of the much higher pressure of the gas from the converter compared to the ambient.

While a diagram of a single adsorber operated batch wise could be drawn, this is elementary; and its operation will be obvious from the description below to those familiar with the adsorption operation. Also no figures are drawn to indicate the many well known variations of such, so called continuous adsorption operation as those of FIGS. 1 and 2, which also may be used to implement this invention.

REGENERATION OF ADSORBENT BEDS BY DIRECT TRANSFER OF HEAT

FIG. 1 shows one of the various flow sheets of vapors and liquids to accomplish the dehydration by adsorption of water away from methanol and indeed away from the other components of the gas stream leaving the converter of a methanol synthesis plant. Modifications of this adsorption flow sheet familiar to the art, may also be used by this process to separate the water present in hot methanol vapors and other constituents of other gas streams, and using the sensible heat of the gaseous stream to regenerate the adsorbent through evaporating therefrom the water which has been adsorbed.

The hot gases from the methanol synthesis converter pass through line 101, and heat exchanger 102. This may be a steam generator to recover a large amount of the sensible heat in this gas stream, coming principally from the exothermic synthesis reactions which produce methanol. Steam for power and process use thus leaves the steam generator by line 103. Depending on the energy balance, some part of the gases flowing in 101 may by-pass the heat exchanger by a line, not shown, so as to give a higher temperature in the line 104 going to the adsorbers.

FIG. 1 diagrams two identical adsorbers, A and B, in parallel, each with multiple beds charged with a suitable adsorbent-desiccant preferably in pellet form. Both resemble a standard shell and tube heat exchanger, with very large tubes held between standard tube sheets, although other standard arrangements may be used. These adsorbers are used alternately to each other, so that while one is adsorbing water to dehydrate the gas stream, the other adsorber is being regenerated by having the adsorbed water vaporized away from the adsorbent. A third adsorber may be interconnected to this parallel arrangement to allow a spare unit or to allow some flexibility in timing of the shifting from the adsorption to the regeneration sequences of the cycle, or back. Such usage is conventional in adsorption practice.

Assuming that adsorbing beds 107 of A have become charged with water in the previous cycle, then the hot gases substantially at the pressure of the converter pass through lines 104 and 105 to enter the space around the tubes 108 inside the shell of A and to heat the adsorbent particles which are supported by suitable means at the level of the bottom tube sheet. These particles are packed inside several or more metal tubes of large diameter. Heat transferred through the walls of the tubes supplies the heat of evaporation plus the heat of adsorption—often about an equivalent amount—so that the water is desorbed, evaporated, and driven off. These large tubes containing the desiccant may be of any convenient diameter, however, if more than about 12 inches the essential heat transfer is undesirably slow. The hot gases mainly 10–15% methanol vapors as described in U.S. Pat. No. 4,235,799 in admixture with permanent gases and with the small amount of water vapor to be removed leave the shell side of A by line 109.

This gas mixture, now somewhat cooler, passes by way of lines 111 through a heat exchanger 112, which recovers more of their heat, which has not been used in the regeneration of the adsorbent in the beds of A. This heat recovery may be by generation of steam by 112 or the heating of boiler feed water going to steam generator 102. However the most important function of this heat exchanging complex, designated simply as 112, will be the counter current preheating of recycle gas in line 126.

Also the heat exchanging noted in 112 will usually include a final cooling of the gas stream in 111 by an additional flow of cooling water, not shown. It is desired to have as low as practical a temperature for the adsorption of water in the gas stream in 111 by the desiccant in 107 of B.

The gas stream of 111, now further cooled and at a pressure somewhat less than that of the methanol converter passes through line 114 to the bed side of the other adsorber, B, and down through the particles of adsorbent-desiccant in the beds 107. Water is adsorbed from the gas stream, and the dehydrated methanol vapors—with a large amount of permanent gases principally CO, $CO_2$, $H_2$, and others—leaves B by line 116. Then this stream goes through line 117 to pass to the condenser-cooler 118. Here methanol is condensed together with any other condensables. These may be principally higher alcohols in from one to several percent, possibly some dimethyl ether in very small amounts, depending on the particular catalysts and flow sheet of the converter loop.

The liquid and the gas phases leaving 118 pass through line 119 to a separating flash drum 120; and the liquid, principally methanol, discharges from the system through line 121.

All of the process described so far, including this condensation of methanol, preferably has been under the pressure of the converter—or slightly less, due to the drop in pressure through piping and equipment. Any lower pressure down to atmospheric may be maintained—usually less advantageously. Now the liquid methanol and any non-condensable gases dissolved therein pass through a reducing valve in line 121 to discharge at atmospheric pressure.

It may be desirable to discharge this methanol into a second flash drum, not shown, to separate the non-condensable gases, relatively small in amount compared to those separated in 120, which may be dissolved in the liquid condensate. If so, this gas stream may be wasted as part of the gases purged from the system, or it may be recompressed to the pressure of 120 and passed back to line 117 leading to the condenser 118 to condense out the methanol in this gas stream.

The residual syngas and inert permanent gases which are flashed out of the liquid methanol in 120 discharge through line 122, some small part is discharged through the purgeline 123 for other processing or waste as desired. The balance is passed by line 124 to be compressed by compressor, 125 to the pressure of line 126, thence heat exchanger 112, and finally they are passed as recycle back to the methanol conversion loop.

Usually the dehydration-adsorption may be done best in B at a high pressure, not much below that of the converter but at as low a temperature as may be economic to attain. On the other hand, the regeneration process taking place in adsorber A, while B is adsorbing, may be done at a high pressure, somewhat less than that of the converter or it may be done at or near atmospheric pressure. A low pressure in the regeneration, with a high pressure for the adsorption-dehydration allows rapid and complete desorption of water in a pressure-swing (a pressure-differential type of regeneration). This will be assumed for the present example, which depends on both a temperature swing and a pressure swing, although either would suffice. However, since the gas stream 101 has both a very high temperature and a very high pressure compared to the ambient, the pressure swing may also be used. This allows a lower temperature to be attained in 102.

The hot gases coming from the heat exchanger 102, following the converter and passing to the shell side 108, of adsorber A, passes through the wall of the tubes to the desiccant 107 in the adsorber tube-beds and evaporates the water therefrom. This desorption, when done at a low final pressure, e.g., below atmospheric, will allow a lower temperature drop of the hot gases entering at 105 and leaving at 109 because of the great aid to the desorption due to this pressure-swing.

By operating the regeneration in A at as low a temperature drop as possible depending finally on a pressure-swing regeneration, it is possible to have the heat exchanger 102, cool the gas stream to a lower temperature than could be possible if desorption was done at a high final pressure. Thus more heat is recovered in 102; and the cost of the overall operation is reduced.

This water vapor from the regeneration passes through lines 130 and 132 to a condenser-cooler 133, operated preferably at atmospheric pressure. Water previously adsorbed in A, and now being desorbed, is condensed in 133, and discharged through line 134 to a receiving tank 135, with a drainpipe 136; while non-condensable gases are discharged through vent line 137. When no more condensate, water, discharges from 136, suction may be applied to vent line 131 to complete the regeneration of the desiccant, and a small additional amount of water may be received in 135.

If there is syngas of value in the exhaust gases discharging through 137, this line or the discharge of the unit supplying suction may be compressed and recycled back to the converter. This is usually not worthwhile, and this wasted gas may be part of the necessary purge of the system.

Alternatively, before the dessicant side of adsorber A, is depressurized; and at the start of the regeneration of its beds 107, a compressor—not shown—may take a gas stream from line 130 and discharge it back into line 111 or 114, thence to go with the gas stream to adsorber B. This will exhaust the syngas and other gases from the bed side of the adsorber A, and leave the water almost alone in being held in the adsorbent beds 107 of A, since water has been found to be held on the desiccant-adsorbent most firmly of the several constituents of the gas stream coming from the converter.

This same object can be obtained, also before depressurizing the adsorption side of A and the condenser and receiver assembly, by connecting a compressor—not shown on the figure—from the vent 137, to the line 111. Gas under the adsorption pressure is then passed from the adsorption side of A through the cold condenser 133, also 134, 135, and 137, then compressed over a comparatively narrow range of pressure, that due to pipe friction, etc. and passed through lines 111 and 114 to the adsorber, B.

When the adsorber side of A is thus "degassed," the pressure there may be allowed to fall, with vent 137 open to the atmosphere. Meanwhile water vapor is desorbing from the beds 107, in the adsorber side of A and is being condensed in 135 and discharged from 136. The last of the water may be stripped out, with valve on line 136 closed, by use of this compressor as a vacuum pump discharging to atmospheric pressure; and the last of the water will be collected in 135 as a vacuum receiver. The adsorbent-desiccant in 107 of A, is thus completely stripped of water, while that in 107 of B has become completely charged with water.

This marks the end of a cycle; and by proper manipulation of the valves (i.e. the change of all those full open to full closed and vice versa.) the operation with A becomes that of adsorption and that with B is that of desorption. For B to act as the desorber, hot gases from line 104 pass through the now open valve 106, and lose some heat and reduced in temperature in going through 108 of B, next line 110 with its now open valve, then through line 111, the now open valve 113, the desiccant in 107 of A, and out—free of water—through now open valve 115 to pass through line 117 and successive steps as before. Cycle after cycle is accomplished through manual or automatic opening and closing of these valves to control the flow of the several gas and liquid streams.

In pressure, the higher than atmospheric in the methanol catalytic converter loop may be from 750 psi to 7500 psi or even more, to which this adsorption-separation system may be attached as an integral part. A large part of the gas necessarily is recycled after the adsorption-separation, and after condensing out the methanol, particularly, also separately, the water. Thus it will be apparent that insofar as the recycle gas is concerned, if the adsorption is done under full pressure, the separation may be accomplished without a substantial loss of pressure between the gas taken from the methanol loop and the large part of it which is returned.

Regeneration of Adsorbent Beds by Circulating a Hot Gas

FIG. 2 shows another flow sheet of the water being separated by the process of the invention. Here a hot inert gas is used as the means of supplying heat to the adsorbent-desiccant for the regeneration or desorbing operation of removing water. Heat transfer is slow through the walls of the container for the adsorbent in FIG. 1 and particularly through the bed itself. Thus the container cannot have a large diameter, and the temperature difference from gas to an average particle in the bed must be large to accomplish the heating for regeneration in a reasonable time.

Instead of heat transfer from outside the bed, a heated inert gas may be circulated directly through the bed to heat and simultaneously to purge water from the particles of adsorbent. This gas may be by-product nitrogen from the air separation plant making oxygen, if the synthesis gas to make methanol is produced by partial oxidation of a carbonaceous fuel. Or it may be carbon dioxide in those plants removing carbon dioxide from the syngas, Syngas itself has been found to be suitable for use; but it would lose a part of its water, and would then have to be recycled to the adsorber for removal of the balance. Indeed also the gas in the stream following the condensation out of the methanol may be used as heat carrier in this separating process. This may be called the "spent" gas and might be obtained from a draw-off connection to line 223 or line 225 or line 226 in FIG. 2, now to be explained. This would be connected to the inert gas inlet at 250. Use of syngas if anhydrous or of this spent gas adds no new component to the system of the circulating gases. An additional advantage will be that either may be at nearly the pressure of the system and thus does not require substantial compression in its use, if desorption is done under high pressure.

The operation of much of the adsorption side of the flow sheet of FIG. 2 duplicates that of FIG. 1. However, the beds for adsorbent may be much larger in diameter and the adsorbent is filled inside the walls of large cylindrical vessels A and B, which are provided with suitable conventional supports for the adsorbent.

Here again the valves are indicated as being in the appropriate open or closed positions for operation of B as adsorbing and A being regenerated.

Thus, the gas stream coming from the methanol converter, enters at 201, passes through the heat recovery exchanger, preferably a steam generator 202, through a second exchanger 260 which preheats the regenerating gas and via line 204, heat exchanger 212, and lines 211 and 214 to enter the adsorbent bed 207, of B.

Water is adsorbed in the bed 207 of B, the dehydrated gas stream passes through lines 216 and 217 to the condenser-cooler 218; the condensate, methanol drains to receiver 220, then through line 221 to storage. The dehydrated and demethanolized spent gas is separated in 220. Some part is purged from the system by line 223; and a part of this may be used as regenerating gas by a line, not shown, connecting to 250. The balance of the stream leaving 220 is compressed by 224 back to converter pressure (to compensate for the pressure drop of the adsorbing part of the cycle). This stream then passes through line 226 and is reheated by heat exchangers 212 and 202 on its way back as recycle to the converter via line 225.

This passage of the product gas from the converter is continued until the adsorbent 207 of B is fully charged with water, when a cutover of B to regeneration by desorption is made through proper adjustment of valves.

Meanwhile adsorber A has been operating on its desorption half of the cycle. The desorption gas system has been charged with inert gas. This is preferably a part of the stream in line 223 or line 226 supplied by a line not shown. The inert gas enters through supply line 250. It then passes through line 252 and compressor 253 which essentially makes up for the pressure drop in circulating the desorbing gas through the system. Usually the absolute pressure will be at or near atmospheric during most of the desorption operation, but it may be at any desired pressure including a partial vacuum.

Desorbing gas goes through line 254 and is heated in heat exchanger 255 by the desorbing gas charged with water—or bypassed 255 by line 256 (dashed)—then through line 257 to be heated further in 260 by incoming gas from the converter or by-passed 260 through line 259. Now at an elevated temperature, the gas stream passes through line 251 to pass by line 262 to adsorber A and its bed 207 of adsorbent. Here the gas stream evaporates the water and picks it up as vapor, is cooled somewhat thereby leaves by line 230, and passes via line 232, heat exchanger 255, then to water-cooled condenser-cooler 233 where water is condensed. This and non-condensed gases pass to separator tank 235 from which water is discharged from 236.

When the water thus is removed from bed 207 of A which has been well heated, the same stream cycle may be used to cool 207 of A, by bypassing the heat exchangers 255 and 250 through lines (dashed) 256 and 259. Thus the desorbing stream, cooled by condenser-cooler 233 passes the route 235, 253, 254, 256, 257, 259, 251, 262, through bed 207 of A and circulates back through 230, 232, 233, 234, and 235 until the bed A is cooled. At that time, there may be connected, if desired, a vacuum pump to line 261 to exhaust the desorbing gas and to reduce the pressure of bed 207 of A.

When anhydrous syngas for the methanol production is used in this way, and it is desired to use syngas for desorption, this relatively small amount can be added to or taken from the stream used in methanol production without substantial effect. If the inert gas is taken from line 223, as is often preferable, the gas may be discarded from the system, or returned to the gas purification plant for recovery of its values.

The cycle is complete, and the operation of A is now changed to adsorption and of B to desorption, with a continuing sequence of alternations of adsorption and desorption in the respective beds, by proper manipulation of the valves. When B is operated as the desorber, the hot gas for desorption in line 251 enters B and its bed of desiccant by line 263, while the incoming gas stream from 211 is dehydrated by the desiccant in bed 207 of A, and is passed, anhydrous, out through 215 and 217 to the subsequent steps as before.

The use of a separate gas for cooling after desorption as well as heating for desorption has the advantage of excellent heat transfer to or from the gas, from or to the adsorbent particles; and the additional advantage, in this case, where water is being desorbed, is that if some of this adsorbate is lost by not being entirely removed from this gas stream, it has no value. This may be different from the usual recovery of solvents by adsorption.

I claim:

1. In the process of dehydrating by adsorption on solid particulate desiccant, of water vapor from a hot gas stream containing methanol vapors and water vapors initially at a temperature of 300° C. to 500° C. and a pressure higher than atmospheric, wherein all of the mechanical and thermal energy required in said process of dehydrating by adsorption is obtained from said gas stream due to its high temperature and high pressure relative to ambient conditions.

2. In the process of claim 1 wherein said hot gas stream comes from a catalytic converter of syngas to methanol.

3. In the process of claim 1 the use of two adsorbers, a first and second, wherein the desiccant in the first adsorber is adsorbing and removing the water from said gas stream after said gas stream is cooled from its first higher temperature; and the desiccant charged with water in the second adsorber is being desorbed by being heated to a temperature higher than that in said adsorbing process in said first adsorber, said heat coming from that in said hot gas stream, so that water previously adsorbed in said second adsorber will be desorbed and evaporated from said second adsorber.

4. In the process of claim 3 wherein the heat required to heat said desiccant in said second adsorber so as to desorb said previously adsorbed water is supplied by heat transfer from said hot gas stream through the walls of a container of said desiccant therein to said particles of said desiccant.

5. In the process of claim 3 wherein the heat required to heat said desiccant in said second adsorber so as to desorb said previously adsorbed water is supplied by contacting said desiccant particles in said second adsorber with a stream of inert gas which has had transferred to it some of the heat which was contained in said hot gas stream.

6. In the process of claim 5 wherein said inert gas is carbon dioxide.

7. In the process of claim 5 wherein said inert gas is nitrogen.

8. In the process of claim 5 wherein said inert gas is syngas purified and ready to be passed into a converter to produce methanol.

9. In the process of claim 5 wherein said inert gas is the residual and spent gas of said process of dehydrating by adsorption from which the water and methanol have been substantially removed.

10. In the process of claim 3 wherein said gas stream at a pressure above atmospheric after being dehydrated in the first adsorber containing a first bed of desiccant at said pressure is passed to the second adsorber containing a second bed of desiccant charged with water at a lower total pressure and therefore lower vapor pressure of water adsorbed therein, so that said water will be desorbed and evaporated from said second bed of desiccant into said gas stream.

11. In the process of claim 3 wherein water is ultimately seprated out by a cooler-condenser as a liquid condensate from a gas stream, and methanol is ultimately separated out by a cooler-condenser from a gas stream as a liquid condensate, substantially anhydrous but containing at least some of the liquid impurities coproduced in the conversion of syngas.

12. In the process of claim 11 wherein said desiccant in said second adsorber after being desorbed of water and prior to being used again to adsorb water is cooled by a stream of gas, said stream of gas having been previously cooled by passing through said cooler-condenser for said methanol vapors.

13. In the process of claim 11 wherein said desiccant in said second adsorber after being desorbed of water and prior to being used again to adsorb water is cooled by a stream of gas, said stream of gas having been previously cooled by passing through said cooler-condenser for said water vapors.

14. In the process of claim 1 wherein said hot gas stream has part of its initial heat removed as a first step by heat transfer to water which is boiling to give steam.

15. In the process of claim 14 wherein said hot gas stream comes from a catalytic converter of syngas to methanol and at least part of said stream is used to generate power, said power being used by at least some of the several elements and components of said manufacture of said syngas used in said converter to methanol, and of said dehydration operation.

16. In the process of claim 1 wherein the solid particulate desiccant is a zeolite which is an alumino-silicate with alkali metal cations, known as a molecular sieve.

17. In the process of claim 1 wherein the solid particulate desiccant is anhydrous calcium sulfate, called anhydrite.

18. In the process of claim 1 wherein the solid particulate desiccant is activated aluminum.

19. In the process of claim 1 wherein the solid particulate desiccant is a silica gel.

20. In the process of claim 1 wherein said hot gas stream contains 0.5 to 12% as much water by weight as methanol, and said desiccant removes as much as 15% of its weight of said water from said hot gas stream.

21. In the process of claim 1 wherein said hot gas stream, containing from 0.05 to 2% as much water by weight as methanol, has said desiccant remove substantially all of said water until said desiccant has adsorbed up to 15% of its weight of said water from said hot gas stream.

* * * * *